(12) United States Patent
Ratcliffe (10) Patent No.: US 8,168,963 B2
(45) Date of Patent: May 1, 2012

(54) SYSTEM AND METHODS FOR SELF-DECONTAMINATING A SURFACE

(76) Inventor: William R. Ratcliffe, Thousand Oaks, CA (US)

( * ) Notice: Subject to any disclaimer, the term of this patent is extended or adjusted under 35 U.S.C. 154(b) by 0 days.

(21) Appl. No.: 12/009,473

(22) Filed: Jan. 17, 2008

(65) Prior Publication Data

US 2008/0286145 A1  Nov. 20, 2008

Related U.S. Application Data (60) Provisional application No. 60/881,200, filed on Jan. 19, 2007.

(51) Int. Cl.
*A46B 15/00* (2006.01)

(52) U.S. Cl. ...... 250/504 H; 15/105; 433/29; 422/186.3

(58) Field of Classification Search .............. 422/22, 422/24, 186, 186.3; 433/29; 15/105; 250/504 H
See application file for complete search history.

(56) References Cited

U.S. PATENT DOCUMENTS

| | | | |
|---|---|---|---|
| 5,650,126 A | 7/1997 | Taoda et al. | 422/122 |
| 5,921,251 A * | 7/1999 | Joshi | 132/112 |
| 6,024,929 A | 2/2000 | Ichikawa et al. | 422/186 |
| 6,094,767 A | 8/2000 | Iimura | |
| 6,099,813 A | 8/2000 | Gipson, II | 422/300 |
| 6,135,126 A | 10/2000 | Joshi | 132/308 |
| 6,242,752 B1 | 6/2001 | Soma et al. | 250/504 R |
| 6,242,862 B1 | 6/2001 | Kawakatsu | 313/634 |
| 6,343,400 B1 | 2/2002 | Massholder et al. | |
| 6,623,272 B2 | 9/2003 | Clemans | 433/215 |
| 6,675,425 B1 * | 1/2004 | Iimura | 15/105 |
| 6,827,910 B2 | 12/2004 | Chen | 422/186.07 |

FOREIGN PATENT DOCUMENTS

| | | |
|---|---|---|
| JP | 2004188214 | 7/2004 |
| JP | 2006167396 | 6/2006 |
| KR | 20040066055 | 7/2004 |
| TW | 595480 | 6/2004 |
| TW | M247180 | 10/2004 |
| WO | 9963859 | 12/1999 |
| WO | 2004012621 | 2/2004 |

OTHER PUBLICATIONS

U.S. Patent Application Publication No. 2003/0071790 A1; Cheng; Apr. 17, 2003.
U.S. Patent Application Publication No. 2004/0053190 A1; Lin; Mar. 18, 2004.
U.S. Patent Application Publication No. 2004/0224145 A1; Weir et al.; Nov. 11, 2004.

(Continued)

*Primary Examiner* — Sean E Conley
(74) *Attorney, Agent, or Firm* — Fitch, Even, Tabin & Flannery, LLP (57) ABSTRACT

A system for self-decontaminating a surface of an object is disclosed herein. The system includes a light emitting member and photocatalytic material which can be mounted on or within the object to be decontaminated. Activation of the system releases an oxidizing agent effective in deactivating chemically or biologically active agents at or near the surface. The system is robust, non-destructive, can be activated on demand, and does not require regeneration or expose a user to harmful materials such as UV irradiation. Also disclosed are objects containing the system, methods for self-decontaminating objects using the system, and methods for fabricating self-decontaminating surfaces on an object.

17 Claims, 4 Drawing Sheets

OTHER PUBLICATIONS

U.S. Patent Application Publication No. 2005/0191505 A1; Akarsu et al.; Sep. 1, 2005.

U.S. Patent Application Publication No. 2005/0212769 A1; Lin et al.; Sep. 29, 2005.

U.S. Patent Application Publication No. 2005/0249955 A1; Gedeon et al; Nov. 10, 2005.

U.S. Patent Application Publication No. 2006/0245191 A1; Ratcliffe; Nov. 2, 2006.

U.S. Patent Application Publication No. 2006/0261285 A1; Broerman; Nov. 23, 2006.

International Search Report and Written Opinion of the International Searching Authority for PCT/US2008/000648 mailed Feb. 5, 2008.

Office Action and Search Report from the Tawain R.O.C. Intellectual Property Office for App. No. 097102053 issued Apr. 12, 2011.

* cited by examiner

SYSTEM AND METHODS FOR SELF-DECONTAMINATING A SURFACE

CROSS REFERENCE TO RELATED APPLICATION

This application claims the benefit of U.S. Provisional Application Ser. No. 60/881,200 filed on Jan. 19, 2007.

BACKGROUND

1. Field of the Invention

The invention relates in general to decontamination systems, and more particularly to self-decontamination systems.

2. Description of the Related Art

Contamination by harmful biological or chemical agents is a common occurrence in everyday life, and decontamination is often required to render such contaminated objects safe for further handling. Conventional decontamination systems for sterilizing or cleaning objects, typically mechanical or chemical in nature, can be used to decontaminate a variety of objects such as brushes, medical instruments, military equipment, and interior or exterior walls. These systems generally include the application of a decontaminating coating to one or more surfaces on the object, or confinement of the contaminated object in a decontaminating enclosure.

One popular type of decontaminating coating contains photocatalytic material which, when exposed to UV light, generates oxidizing species that degrade biological or chemical agents. Oxidative coatings can be used in a variety of situations, including high efficiency particulate air (HEPA) filters and wall paint.

Photocatalytic oxidation is based on the production of several highly reactive, short-lived chemical species, particularly oxygen-based radicals and ions that are effective in neutralizing or destroying microorganisms and hazardous chemicals such as volatile organic compounds (VOCs). One such reaction product, ozone, has the ability to oxidize organic material, including the cell wall of a microorganism. Ozone is a reactive form of oxygen that is a strong oxidant having documented ability to kill spores, bacteria, and viruses. In addition, since ozone is released into the ambient atmosphere during oxidation, the atmosphere immediately surrounding the coating may be decontaminated at the same time as the coated surface.

Photocatalytic materials can oxidize a wide range of substances and the effectiveness of photocatalytic oxidation systems has been well documented. Photocatalytic particles, coatings, and thin films have, for example, been demonstrated to oxidize (or reduce) a very wide range of organic and inorganic compounds at ambient temperatures, pressures, and humidities. Furthermore, a targeted microorganism is usually completely destroyed during the oxidation process.

Titania exists in a number of crystalline forms, the most important of which are anatase and rutile. The photocatalytic activity of titania results in thin coatings of the material exhibiting self cleaning and disinfecting properties under exposure to UV radiation. These properties make the material a candidate for antimicrobial coatings which potentially may be used to decontaminate many different types of objects, including medical devices, food preparation surfaces, air conditioning filters, sanitary ware surfaces (e.g. toilets, sinks), articles of clothing and the like.

Self-cleaning coatings using photocatalytic titanium dioxide ($TiO_2$) have gained considerable industry attention in recent years. $TiO_2$ offers two unique properties: (a) strong oxidation power, and (b) super-hydrophilicity. The first property, strong oxidation power, can be used to kill bacteria attached to a wall or to oxidize/remove foul smells from stains in a toilet and, as a result, $TiO_2$-coated tile and $TiO_2$-coated glass are now commercially available. The second property, super-hydrophilicity, can be used to provide anti-fogging and self-cleaning properties to optical structures in that, when a $TiO_2$ coating is applied to an exterior surface, it allows dirt and stains to be easily washed away with water or by rainfall. $TiO_2$ microstructures also possess a high refractive index (on the order of about 1.95-1.99) and excellent transparency in the visible range. One popular approach is to apply a coating (e.g. over layer, over material) of $TiO_2$ to catalytically decompose chemical or biological agents on the surface of an object upon irradiation with low level or long wavelength UV light sources, typically sunlight or fluorescent lamps, respectively.

Self-cleaning and/or disinfecting/sterilizing coatings, structures, and systems developed for decontamination are disclosed in U.S. Pat. Nos. 6,827,910; 6,242,862; 6,242,752; 6,135,126; 6,024,929; 6,099,813; and 5,650,126 as well as in U.S. Patent Publication Nos. 2006/0261285; 2005/0249955; 2005/0212769; 2005/0191505; 2004/0224145; 2004/0053190, and 2003/0071790. However, each one of these references suffers from one or more of the following disadvantages: the decontamination process is dependent on sunlight as the UV source (i.e. it can not be used indoors); the decontamination technique requires an enclosed space or structure such as an external housing, or an additional, permanent structural feature such as a cover plate which can alter the dimensions of the surface targeted for decontamination; the approach can be costly and/or have impractical logistical requirements such as access to UV-generating equipment and power (e.g. transporting large, fragile mercury lamps and their associated power supplies to remote locations such as battlefields); human health or safety may be compromised because the user is exposed to and/or in direct contact with UV irradiation or other harmful materials during the decontamination process; the photocatalytic products generated by the coating attack and damage the surface during the decontamination or bleaching process; the procedure requires external ingredients or materials that must be placed in physical contact with the contaminated surface in order to decontaminate it, the system has low efficiency due to its dependence on low level or long wavelength UV light sources, or the system either requires a large or rigid UV lamp as a functional component or a housing containing such a lamp.

Therefore, a need exists for systems and methods for self-decontamination which can be adapted for use, on demand if necessary, in a wide variety of applications and locations. Ideally, such systems should be safe, cheap, robust, non-destructive, portable, and flexible, as well as more efficient, smaller and/or more adaptive than current technologies.

SUMMARY

The present invention is directed to a photochemically-activated system for self-decontaminating a surface on an object. The system includes at least one light emitting member and at least one photocatalytic material or coating which are mounted on or within the object. The photocatalytic material is mounted adjacent to the surface and is optically connected to one or more light emitting members. Activation of the system can release an oxidizing agent effective in deactivating chemically or biologically active agents at or near the surface, or portion thereof, to be decontaminated. The system can be small, safe, non-destructive, robust, and activated on demand, and it does not require regeneration or expose a user to UV irradiation or other potentially harmful materials during use.

The invention also provides objects incorporating the system, methods for self-decontaminating an object having the system, and methods for fabricating self-decontaminating surfaces on an object.

In one aspect, the present invention can provide a system for self-decontaminating at least one surface of an object, the system having at least one photocatalytic material and at least one light emitting member. The at least one photocatalytic material and the at least one light emitting member are mounted on or within the object, the at least one photocatalytic material is optically connected to the at least one light emitting member, and the at least one photocatalytic material is adjacent to the at least one surface. In one embodiment, the object is functionally independent of the system. In another embodiment, the at least one photocatalytic material includes titanium dioxide. In yet another embodiment, the at least one light emitting member provides ultraviolet light. In a further embodiment, the at least one light emitting member provides ultraviolet light having a wavelength in a range of about 180 nm to about 425 nm. In another embodiment, the at least one light emitting member is a light emitting diode. In yet another embodiment, the system further includes adhesive material. In another embodiment, the system can be activated on demand. In a yet further embodiment, the system can be activated by at least one control switch. In another embodiment, the at least one control switch is electrically connected to the at least one light emitting member, and the at least one light emitting member provides a quantity of light to the at least one photocatalytic material upon activation of the at least one control switch. In a further embodiment, the system further includes at least one reflective element which is optically connected to the at least one photocatalytic material and the at least one light emitting member.

In a second aspect, the present invention can provide an object having at least one system for self-decontaminating at least one surface of an object, the system having at least one photocatalytic material and at least one light emitting member. The at least one photocatalytic material and the at least one light emitting member are mounted on or within the object, the at least one photocatalytic material is optically connected to the at least one light emitting member, and the at least one photocatalytic material is adjacent to the at least one surface. In one embodiment, the object can be a brush. In another embodiment, the object can be a holder for a toilet plunger. In yet another embodiment, the object can be a tape measure.

In a third aspect, the present invention can provide a method for fabricating at least one self-decontaminating surface on an object. The method includes depositing at least one photocatalytic material adjacent to the at least one surface and mounting at least one light emitting member on or within the object, wherein the at least one photocatalytic material is optically connected to the at least one light emitting member. In one embodiment, the object is functionally independent of the system. In another embodiment, the method further includes depositing at least one adhesive material adjacent to the at least one photocatalytic material. In yet another embodiment, the method further includes combining at least one adhesive material with the at least one photocatalytic material. In a further embodiment, the method further provides at least one control switch for activating the system. In another embodiment, the at least one photocatalytic material is deposited adjacent to the at least one light emitting member.

In a fourth aspect, the present invention can provide an object having at least one self-decontaminating surface fabricated by depositing at least one photocatalytic material adjacent to the at least one surface and mounting at least one light emitting member on or within the object, wherein the at least one photocatalytic material is optically connected to the at least one light emitting member.

In a fifth aspect, the present invention can provide a method for self-decontaminating at least one surface of an object. The method includes: providing a self-decontaminating system having at least one photocatalytic material and at least one light emitting member; activating the least one light emitting member, thereby inducing the at least one light emitting member to emit light; and irradiating the at least one photocatalytic material with at least one portion of the light emitted by the light emitting member, thereby releasing an oxidizing agent adjacent to the at least one surface of the object. In one embodiment, the light emitting member is a light emitting diode. In another embodiment, the light emitted by the light emitting member includes ultraviolet light. In yet another embodiment, the at least one photocatalytic material includes titanium dioxide. In a further embodiment, the oxidizing agent includes ozone.

DETAILED DESCRIPTION

The present invention is directed to a photochemically-activated system for self-decontaminating a surface on an object. The system can release an oxidizing agent effective in deactivating certain chemically or biologically active agents at or near the surface. The system includes at least one light emitting member and at least one photocatalytic coating which can be mounted on or within a surface of an object requiring decontamination. The invention also provides objects incorporating the system, methods for self-decontaminating an object having the system, and methods for fabricating self-decontaminating surfaces on an object.

The present invention can provide systems and methods for decontamination, particularly self-decontamination, that can be safe, cheap, robust, non-destructive, portable, flexible, more efficient, smaller and/or more adaptive than current technologies.

Other features and advantages of the invention will be apparent from the following detailed description when taken together with the drawings, and from the claims. The following description presents preferred embodiments of the invention representing the best mode contemplated for practicing the invention. This description is not to be taken in a limiting sense but is made merely for the purpose of describing the general principles of the invention whose scope is defined by the appended claims.

Before addressing details of embodiments described below, some terms are defined or clarified. As used herein, the terms "comprises," "comprising," "includes," "including," "has," "having" or any other variation thereof, are intended to cover a non-exclusive inclusion. For example, a process, method, article, or apparatus that comprises a list of members or elements is not necessarily limited to only those members or elements but may include other members or elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The following definitions refer to the particular embodiments described herein and are not to be taken as limiting; the invention includes equivalents for other undescribed embodiments.

As used herein, the term "adjacent to" when referring to a layer or coating on a surface, or to atmosphere adjoining a surface, does not necessarily mean that the layer, coating or atmosphere is immediately next to the surface; there may or may not be another contiguous or non-contiguous layer or material present between the layer, coating or atmosphere and the surface.

As used herein, the term "adjoining atmosphere" when referring to a surface or portion thereof targeted for decontamination is intended to mean the atmosphere immediately surrounding and which lies in relatively close proximity to the surface, including without limitation next to or in contact with the surface.

As used herein, the term "biological agent" is intended to mean one or more biological organisms and/or their byproducts including without limitation viruses, bacteria, and parasites in any form (including spores) as well as biologically generated toxins.

As used herein, the term "chemical agent" is intended to mean a hazardous chemical species or compound including without limitation chemical warfare agents and hazardous industrial compounds.

As used herein, the term "coating" is intended to mean one thickness, course, or fold laid or lying over or under another layer or support. The coating may be contiguous or non-contiguous, including without limitation coatings which are uniform, patterned or sprinkled, and may contain more than one type of material; equivalent terms—over layer, over material.

As used herein, the term "control switch" is intended to mean any suitable means for activating a source of illumination such an ultraviolet lamp on demand, including without limitation a toggle switch on an object or connected to an object via remote control.

As used herein, the term "decontaminate" or "decontaminating" when referring to an object or surface is intended to mean devitalizing, deactivating or ridding part or all the object or surface of contamination after exposure to one or more toxic agents, including without limitation chemical or biological agents and by-products thereof. An agent or by-product may be devitalized or deactivated in a number of ways including, without limitation, oxidation, disinfection or decomposition. Non-limiting examples of decontamination methods include sterilization, sanitization, deodorizing, and the use of disinfectants.

As used herein, the term "depositing" or "deposition" when referring to depositing materials on a surface is intended to mean any viable method of deposition including without limitation layering, sprinkling, beading, extruding, patterning, spraying, brushing, rolling, pouring, spin coating, dip coating, ink jet printing, sol-gel processing or application of a preform.

As used herein, the term "device" is intended to mean a piece of equipment or a mechanism designed to serve a special purpose or perform a special function.

As used herein, the term "deactivate" or "deactivating" when used to describe a biological or chemical agent is intended to mean that the agent is destroyed, rendered totally inactive, or made substantially less effective.

As used herein, the term "film" is intended to mean a thin covering, material, or coating.

As used herein, the phrase "functionally independent" when referring to an object is intended to mean that the object can perform one or more of its typical functions in either the presence or absence of a self-decontaminating system or method according to the invention.

As used herein, the term "lamp" when used to describe a light emitting member is intended to mean any of various devices for producing light or one or more light emitting components thereof, including without limitation a light emitting diode, a light wire containing a plurality of LEDs, and a glass bulb or tube that emits light produced by electricity such as an incandescent lamp or fluorescent lamp. Representative examples of light emitting members suitable for the invention include without limitation electroluminescent, electroactive, and photoactive devices.

As used herein, the term "mounted" when referring to mounting a photocatalytic material or light emitting member on or within an object is intended to mean the material or member is attached to the object, including without limitation permanent or temporary attachment to an exterior or interior surface or chamber of the object by chemical, physical or mechanical means.

As used herein, the phrase "optically connected" when referring to a photoactive material and a light source or light emitting member is intended to mean that light can be provided to the photoactive material from the light source. Examples of optical connections include without limitation a direct connection through close proximity of the photoactive material to a light source and an indirect connection via an optical wave guide and/or other optical components such as one or more reflective elements.

As used herein, the term "on demand" when referring to activation of a decontamination system is intended to mean that the system can be activated or deactivated at will, including without limitation continual activation, activation at or shortly after the time of exposure to contamination, or deactivation following a period of time after exposure.

As used herein, the term "surface" when referring to an object is intended to mean any exterior or interior surface of the object exposed to the atmosphere, or portion thereof, and the adjoining atmosphere.

As used herein, the term "transparent" or "translucent" when referring to a material or layer is intended to mean the material or layer, or a portion thereof, is light-transmissive.

Attention is now directed to more specific details of embodiments that illustrate but not limit the invention.

Figure 1:
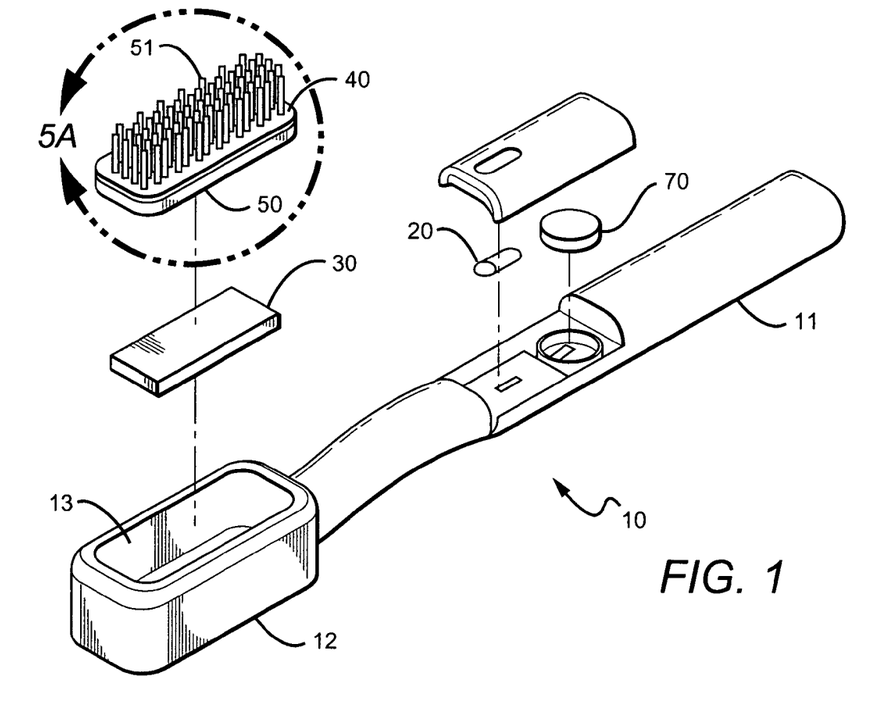
FIG. 1 is an exploded schematic perspective view of a self-decontaminating brush according to one embodiment of the invention where a photocatalytic layer has been deposited above, and in close proximity to, an internal light source mounted on the brush head of the brush.
Figure 2:
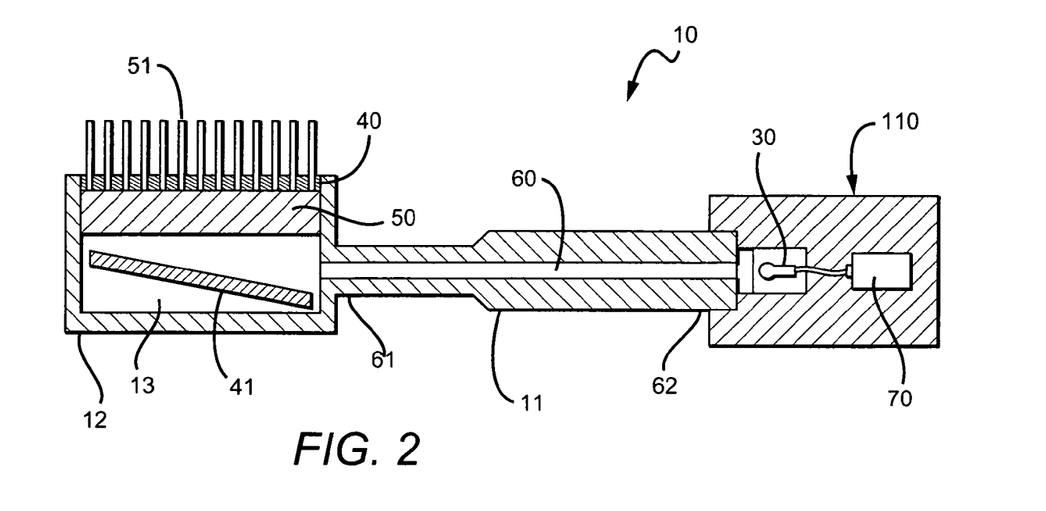
FIG. 2 is a schematic transverse cross section view of a self-decontaminating brush according to one embodiment of the invention having a wave guide which can transmit light emitted from an external light source to the brush head via a reflective surface mounted in the brush head.

FIGS. 1-2 are schematic representations of self-decontaminating brushes according to the invention. FIG. 1 shows an exploded, perspective view of a self-decontaminating brush (10) according to one embodiment. FIG. 2 depicts a simplified cross-sectional view of a brush (10) according to another embodiment. Referring to FIGS. 1-2, the brushes in each of these two illustrated embodiments contain a system for self-decontaminating surfaces on the brush head of a brush and, in each embodiment illustrated, the system includes a photocatalytic coating (40) located adjacent to the brush head (12) and a light emitting member containing one or more light sources (30) such as one or more LEDs.

As shown in the embodiment illustrated in FIG. 1, a light source (30) can be mounted in a recessed cavity (13) within the brush head (12) of a brush (10), such as a toothbrush, a toilet brush, a hair brush or substantially any other brush. The light source (30) can be positioned underneath the support plate (50) holding the bristles (51) on the brush head (12), and a photocatalytic coating (40) containing $TiO_2$ can be deposited directly on top of the support plate (50). In this embodiment, the photocatalytic coating (40) and light source (30) are placed in relatively close proximity to each other within the device in order to ensure that they are optically connected. Also, in order to maintain that optical connection in this embodiment, the support plate (50) should be substantially or completely transparent.

Therefore, upon activating the self-decontaminating system shown in FIG. 1, the light source (30) in the brush (10) can illuminate the photocatalytic layer (40) on the support plate (50) containing the bristles (51), thereby generating ozone in and around the photocatalytic material. The ozone generated can decontaminate nearby structures on the brush head (12), including the support plate (50) and bristles (51) thereon, and the adjoining atmosphere. The brush (10) illustrated in FIG. 1, therefore, can self-decontaminate surfaces on its own brush head (12). The system in this embodiment can be activated by any suitable means capable of turning on the light source, including without limitation a turning on the light source, including without limitation a control switch (20) on the handle (11) of the brush (10), and any suitable power supply can be used including without limitation a battery (70) located in the handle (11), as illustrated in FIG. 1.

Many variations of the brush illustrated in FIG. 1 are within the scope of the present invention. In one embodiment, the photocatalytic coating can be deposited inside the light source such as, for example, on the backside (underside) of the top of the light source, which is typically a layer of transparent material such as glass, plastic or epoxy. In another embodiment, photocatalytic material may be incorporated into one or more active materials or layers of a UV light source, including without limitation an organic light emitting diode (OLED), such that the light source itself can generate ozone. In a further embodiment, the photocatalytic material (40) may be coated on or embedded in the bristles (51) on the brush head (12).

The function(s) of the object can be independent of, and unaffected by, the self-decontaminating system, as illustrated by the embodiments discussed above. However, the light emitting member and/or the photocatalytic material may be a functional component of the object, as well as the self-decontaminating system, in other embodiments.

FIG. 2 illustrates another embodiment of the invention in which light from a remote, detachable UV light source can be provided to a photocatalytic layer on the brush head. In this embodiment, a wave guide (60) spanning the length of the brush (10) can transmit UV light from an external UV light source (30) to a photocatalytic layer containing $TiO_2$ (40) underlying the brush head (12) via a reflective element (41). The UV light source (30) in this embodiment may be located in any suitable location external to the brush head (12), including without limitation in an external device such as a support (cradle) or charging device (110), as illustrated in FIG. 2. The light emitting UV light source (30) in this embodiment can be temporarily mounted onto the brush (10) by placing the brush (10) in an external charging device (110), thereby automatically aligning the wave guide (60) with the light source (30) and activating the self-decontamination system. The light from the illuminated light source (30) can then travel from the end (62) of the brush handle (11) nearest the charging device (110), via the wave guide (60), to the end (61) of the brush handle (11) farthest from the charging device (110) and into the brush head cavity (13). The UV light entering the brush head cavity (13) can then be reflected upwards by a reflective element (41) such that it can irradiate the photocatalytic layer (40) and thereby generate ozone. After a period of time sufficient to decontaminate the brush head, the brush (10) can then simply be removed from the charging device (110) in order to deactivate the system. In another embodiment, the charging device may contain a control switch for the system. In yet another embodiment, the light source (30) may be located within the handle (11) of the brush (10). In another embodiment, the photocatalytic material (40) may be coated on or embedded in the bristles (51) on the brush head (12).

The reflective element (41) may be a high gloss reflecting surface such as a mirror and can contain any suitable reflective material, including without limitation Ni. Nonlimiting examples of suitable optical wave guides include an optical fiber and a rectangular waveguide.

Different types of configurations may be used for activating the self-decontaminating system as needed, including both manual and electrical control mechanisms. The system can therefore be designed to activate in a manner appropriate for a particular application, including without limitation activation on demand or for continuous use. In one embodiment, an internal control switch (20) can be located on the handle (11) of a brush, as illustrated in FIG. 1. A control switch may be activated by connection to any suitable power supply, including without limitation a rechargeable battery. In another embodiment, a control switch may be located in a separate device, including without limitation a cradle or charging device. A control switch can be used to activate the system on demand, including turning the system on and off at appropriate times/intervals in order to minimize or prevent exposure of sensitive bodies or surfaces such as skin to potentially hazardous UV irradiation and to save energy when decontamination is not needed. In yet another embodiment, the system may include a timing circuit or other type of timer. The system may also be designed to be automatically activated (i.e. without a control switch) by any suitable means, including without limitation placing the brush in a cradle or charging device (110), as illustrated in FIG. 2, or by mounting a charging device on the object.

Any suitable external or internal power supply, or connection thereto, can be used for the invention including without limitation an electrical outlet (e.g. AC socket), drive circuitry, or battery capable of providing an appropriate voltage to the system either directly or indirectly (e.g. via a charging cradle or other type of external or internal adaptor). The power supply can be located anywhere on or within the object as long as it does not significantly impede the function of the object and provides sufficient power to the system to self-decontaminate the object. The battery in the handle of the embodiment shown in FIG. 1, for example, may be located in the head of a brush, along with the photocatalytic material and the light source, in other embodiments.

Many different types of photocatalytic materials may be suitable for the invention depending upon the application of interest, including without limitation titanium dioxide ($TiO_2$). For optimal performance, the relative index of refraction of the photocatalytic material should match that of the light emitting member.

Light sources other than sunlight and mercury lamps show promise for use in decontamination systems. UV light emitting diodes (LEDs), for example, can offer many benefits over sunlight and mercury lamps as sources of UV irradiation. LEDs can be "instant-on", potentially much cheaper, easily portable, and have a higher theoretical efficiency. They can also be smaller and more robust than mercury lamps, and multiple LEDs may be readily bundled into flexible structures such as light wires. UV LEDs have also been demonstrated to sterilize water spiked with bacteria and to disinfect small objects placed within structures (e.g. housings) containing such lamps. Many types of UV light sources may be suitable for use in the invention, including inorganic and organic LEDs.

The light emitting member should emit light in a wavelength range appropriate for photoactivating the photocatalytic material. A system containing $TiO_2$ as the catalytic material, for example, may contain a UV light emitting member, including without limitation one that emits UV light with a wavelength in the range of about 180 nm to about 425 nm. A variety of types of light emitting members can be suitable for the invention, depending on the nature of the surface to be decontaminated, including without limitation one or more independent light sources such as UV LEDs, a light wire containing one or more light sources such as UV LEDs, a light guide that can transmit light such as UV light from a remote light source, or a laser such as a UV laser (e.g. if a UV light source is located in a housing or other type of enclosure).

A variety of techniques can be used to mount the light emitting member at, within, or near the surface of interest, including without limitation soldering, ultrasonic bonding, double sided tape or conductive adhesive. One nonlimiting example of conductive adhesive is conductive epoxy.

Figure 3A:
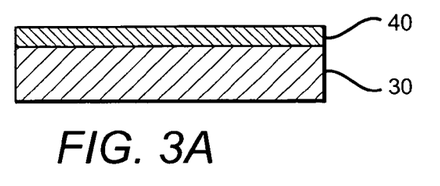
FIG. 3A is a schematic transverse cross section view of one embodiment of the invention having a light source coated with a contiguous layer of photocatalytic material.
Figure 3B:
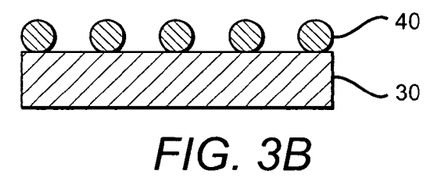
FIG. 3B is a schematic transverse cross section view of one embodiment of the invention having a light source coated with a non-contiguous, beaded layer of photocatalytic material.
Figure 3C:
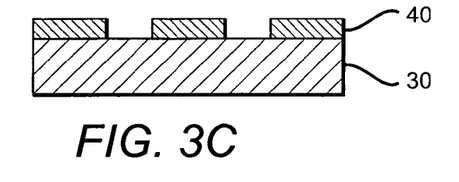
FIG. 3C is a schematic transverse cross section view of one embodiment of the invention having a light source coated with a non-contiguous, patterned layer of patterned photocatalytic material.

The photocatalytic material/coating in the system can be prepared by blending the photocatalytic material (typically as a fine powder) and a suitable solvent to form slurry, and then depositing the slurry adjacent to the surface of an object. Solvents suitable for use with the invention include without limitation organic solvents and water-based solvents for polymeric materials such as paints. FIGS. 3A-3C illustrate three exemplary methods of depositing photocatalytic material adjacent to a surface. In one embodiment, photocatalytic material (40) can be deposited as a single and contiguous layer on the surface of a light source (30), as shown in FIG. 3A. In another embodiment, photocatalytic material (40) can be deposited on a light source (30) as a plurality of non-contiguous beads, as shown in FIG. 3B. In yet another embodiment, photocatalytic material (40) may be deposited as a non-contiguous patterned layer during deposition on a light source (30), as shown in FIG. 3C.

The optimal thickness of the photocatalytic coating will be dependent upon the photocatalytic materials used, the type and positioning of the light emitting member, and the nature of the surface to be decontaminated. The coating can be solidified and/or attached to the surface by any suitable means, including without limitation having the material cast, pressed into a pellet, or cured by air, heat, or UV irradiation.

Figure 4A:
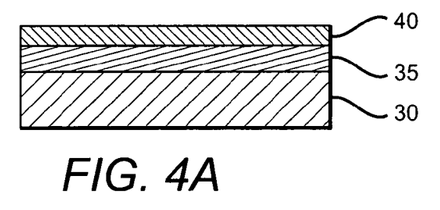
FIG. 4A is a schematic transverse cross section view of one embodiment of the invention showing a light source coated with a contiguous bilayer containing a layer of adhesive material adjacent to a layer of photocatalytic material.
Figure 4B:
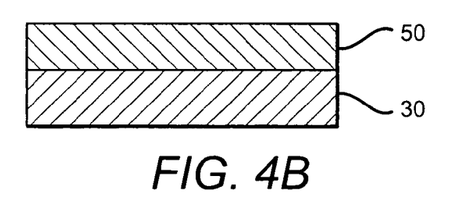
FIG. 4B is a schematic transverse cross section view of one embodiment of the invention showing a light source coated with a contiguous, blended layer of adhesive material and photocatalytic material.

The system may also contain adhesive material which binds the photocatalytic coating to a surface, as shown in FIGS. 4A-4B. In one embodiment of the invention, the adhesive material (35) can be deposited as a layer on the surface of a light source (30) and the photocatalytic material deposited as a contiguous layer (40) adjacent to the adhesive layer, as shown in FIG. 4A. In another embodiment, the adhesive material may be blended with the photocatalytic material prior to deposition, and then deposited (e.g. extruded) as a single composite layer (50) on a surface such as a light source (30), as shown in FIG. 4B. Adhesive materials suitable for the invention include without limitation epoxy, plastic, and adhesive film or tape. The optimal thickness of the adhesive material will be dependent upon the adhesive and/or photocatalytic materials used, the type and positioning of the light emitting member, and the nature of the surface to be decontaminated. For optimal performance, the relative index of refraction of the adhesive material (35) or composite adhesive-photocatalytic material (50) should match or substantially match that of the light source (30). The adhesive material can be cured, if necessary, by any standard means for solidifying the composition which does not affect the activity of the adhesive or photocatalytic material, including without limitation the use of inherent properties of the adhesive material or external manipulations such as air drying, heat, pressure, UV irradiation, and combinations thereof. In one embodiment, for example, the adhesive may be cured by activating a light emitting member in the self-decontaminating system.

Photocatalytic and adhesive materials suitable for use with the invention may be transparent or translucent with respect to the wavelength of the light source (e.g. transmissive to UV light if the light source is a UV light source), and sufficiently porous (i.e. breathable) to let in the water, oxygen, or other reagents required for photocatalysis. Several suitable oxidizing agents can be provided by the system, depending upon the nature of the photocatalytic material present, including without limitation those containing one or more oxidizing species such as ozone. In addition, the self-decontaminating system should generate a sufficient concentration of oxidizing agent to sterilize the surface adjacent to the photocatalytic material/coating. In practice, for systems generating only ozone as the oxidizing agent, at least about 1 μmoles of ozone may be required for the system of operate effectively. Furthermore, since the gaseous ozone diffuses away from the surface with time, certain embodiments of a self-decontaminating system may be more effective when placed in an enclosure such as a cutlery drawer or tight-fitting housing (e.g. pen, door knob, brush, or measuring tape).

Figure 5A:
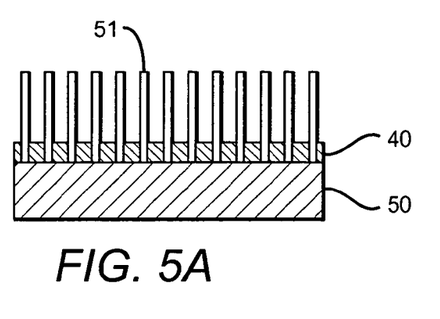
FIG. 5A is a schematic transverse cross section through the embodiment of the invention shown in FIG. 1 having the bristle support in the brush head coated with a contiguous layer of photocatalytic material.
Figure 5B:
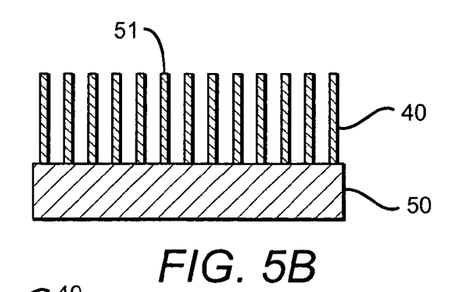
FIG. 5B is a schematic transverse cross section view through one embodiment of the invention showing a brush head having bristles that are impregnated with photocatalytic material.
Figure 5C:
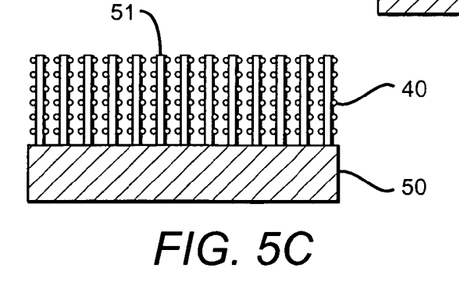
FIG. 5C is a schematic transverse cross section view through one embodiment of the invention showing a brush head having bristles on which a non-contiguous, beaded layer of photocatalytic material has been deposited.

The photocatalytic layer may be applied to any suitable surface on the object where it can be optically connected to an appropriate light source. FIGS. 1, 2 and 5A illustrate non-limiting embodiments in which the bristle support (50) in the brush head (12) of a brush (10) may be coated with a contiguous layer of photocatalytic material (40). In another embodiment, the bristles (51) of the brush head can be impregnated with photocatalytic material (40), as illustrated in FIG. 5B. In yet another embodiment, a non-contiguous layer of photocatalytic material (40) may be deposited on the bristles (51) of the brush head, as illustrated in FIG. 5C where beads of photocatalytic material (40) are deposited on the surface of one or more bristles (51).

Figure 6A:
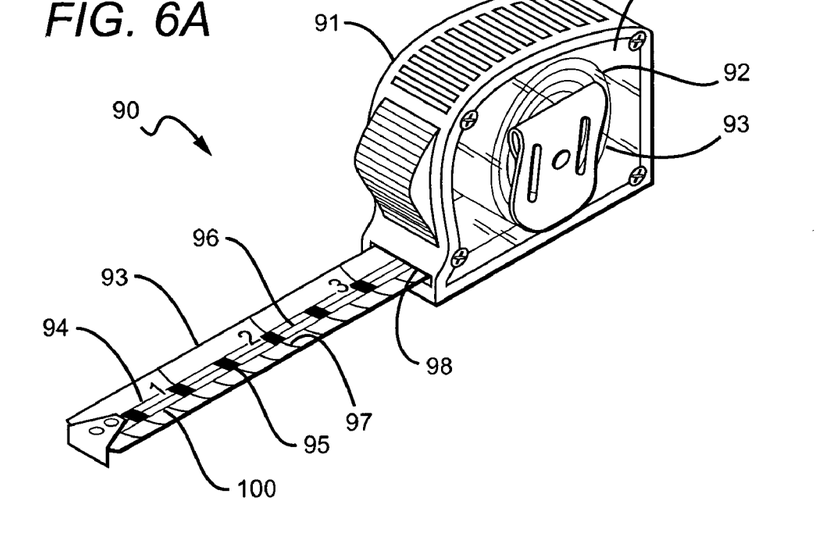
FIG. 6A is a schematic perspective view of one embodiment of the invention showing a self-decontaminating tape measure having a self-sterilizing measuring tape.
Figure 6B:
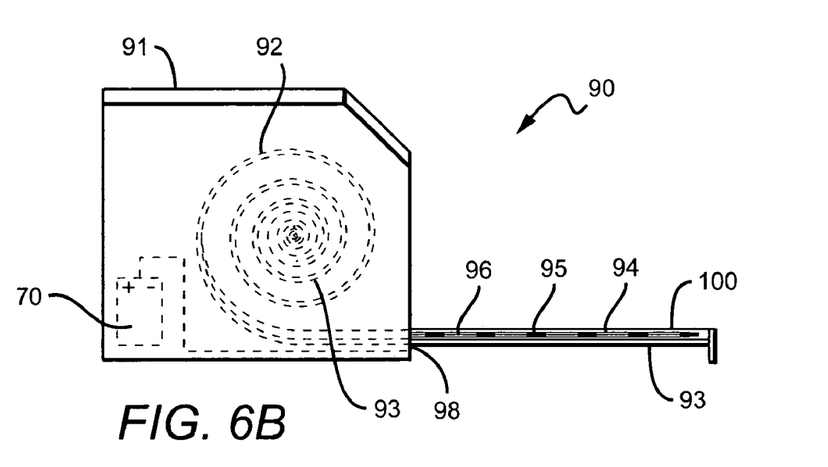
FIG. 6B is a schematic transverse cross section view of the embodiment shown in FIG. 6A.
Figure 6C:
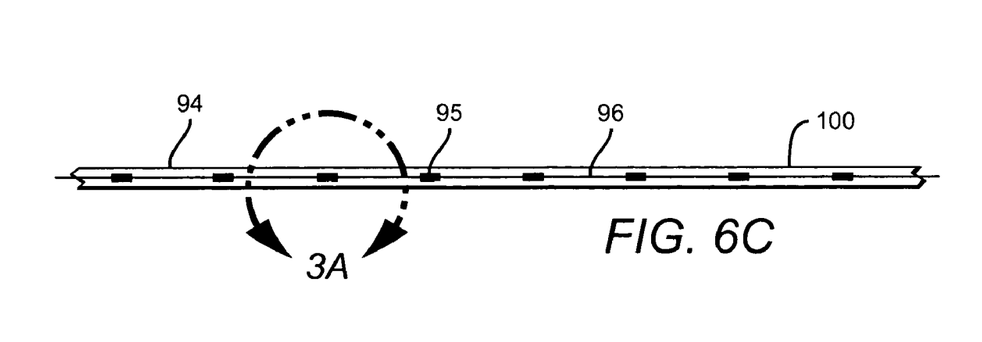
FIG. 6C is a schematic transverse cross section view of the light wire (94) shown in FIG. 6A.

FIGS. 6A-6C are schematic representations of one embodiment of a self-decontaminating tape measure according to the invention, a tape measure having a retractable, self-sterilizing measuring tape. In this embodiment, the tape measure (90) can include a housing (91) with a rotatable spool (92) mounted therein. A length of illuminable tape (93) can be wound upon the spool (92). A light wire (94) containing a string of LEDs coated with a photocatalytic material (95) can be mounted on the top side of the measuring tape (93). The coated LEDS (95) in the light wire (94) can be electrically connected to each other or and/or to a power supply in any suitable manner, including without limitation by electrical wires or wiring (96). In another embodiment, the light wire (94) may be attached to the tape measure (90) via transparent or substantially transparent epoxy. In yet another embodiment, the light wire (94) may be mounted on the underside of the measuring tape.

The illuminable tape (93) can also include a linear measuring scale (97) printed thereon. The illuminable tape (93) may be pulled from the housing to expose the linear measuring scale (97) and the light wire (94). The housing (91) may include a partially, substantially, or completely transparent portion (98) allowing light emitted from the illuminable tape (93) to illuminate and/or escape the housing (91) in some embodiments. In other embodiments, the housing (91) can be opaque and the system may be activated when the tape (93) is retracted into the housing. The tape aperture (98) can be dimensioned to allow the illuminable tape (93) to pass through the aperture (98) as the user pulls the illuminable tape (93) from the housing (91). The housing (91) may also include a power supply for illuminating the LEDs (95), including without limitation a battery (70) which may be electrically connected to the LEDs (95). Alternatively, the LEDs (95) can be illuminated by providing an electrical connection to an external power supply, including without limitation a connection to a power supply via a charging cradle or other type of adaptor connected to an electrical outlet/drive circuitry and capable of providing an appropriate voltage to the system.

One non-limiting example of a light wire (94) structure suitable for the invention is illustrated in FIG. 6C. This embodiment includes multiple LED light sources having a photocatalytic coating (95), as illustrated in FIG. 3A. The LEDs are electrically connected by wires (96) and surrounded by an external casing (100). The embodiment illustrated may include a polymer ribbon (casing) having one or more apertures that can each receive an LED (95). In one embodiment, the wires (96) can be wirebonded along the ribbon and, when they reach an LED (95), can be wirebonded to the LED (95). In another embodiment, the LEDs (95) may have a portion missing, such that both electrodes on the LED (95) can be accessed from one side. Several exemplary light wire configurations suitable for the invention are disclosed in U.S. patent application Ser. No. 11/453/470. The light wire may be attached to the tape using any suitable means including clear epoxy, which can provide physical integrity to the LED as well as a suitably matched index of refraction, or a conformal coating such as a composition containing preformed film and glue. Alternatively, the configuration of the LEDs (95) in the light wire (94) can be rotated by 180 degrees (flipped) such that the photocatalytic layer (40) is sandwiched between the LED light source (30) and the tape (93).

The efficiency of the system and methods of the invention can be optimized by modifying the object as long as the modification does not substantially affect the function of the object. The cavity (13) of the brush head (12) shown in FIG. 1, for example, can be formed in a parabolic shape in order to direct more light upwards towards the photocatalytic material (40) on the brush support (50).

The systems and methods of the invention are highly adaptable and thus should serve a wide range of applications. Objects such as door knobs, walls, combs, hairbrushes, nail brushes, toilet plungers, tape measures and medical instruments are only a few potential applications the self-decontaminating systems of the present invention may be suitable for. Embodiments using one or more LEDs as a light source, for example, can be highly adaptable. LEDs come in a variety of sizes and shapes, the photocatalytic coatings can be deposited in a range of shapes and sizes, and light wires containing multiple LEDs having photocatalytic material, whether inside, outside, or not physically connected to the LEDs, can also be extremely flexible.

Suitable exposure periods for self-decontamination can vary depending upon the object and application. In some embodiments, an exposure time of about 15 minutes to about 30 minutes should be sufficient to for the object to self-decontaminate. The ability to activate the system on demand also ensures that self-decontamination can take place when the object is not in use, such as after a person has finished brushing their teeth, and thus should pose no threat to the safety, health or well-being of the user.

Due to the relative rates of buildup versus diffusion of the active agent produced by the catalytic layer, including without limitation gaseous ozone, the systems and methods of the present invention may be particularly efficient in closed systems. Photocatalytic materials and LEDS can, for example, be strategically placed inside a drawer or within a container in which an object can rest during the decontamination process and, in some embodiments, also for storage purposes. A holder or cover for a toilet brush or toilet plunger, for example, may contain surfaces having photocatalytic material and LEDs, including light wires of sufficient length and flexibility to cover the space needed to decontaminate a brush or plunger after use.

Figures 7A, 7B:
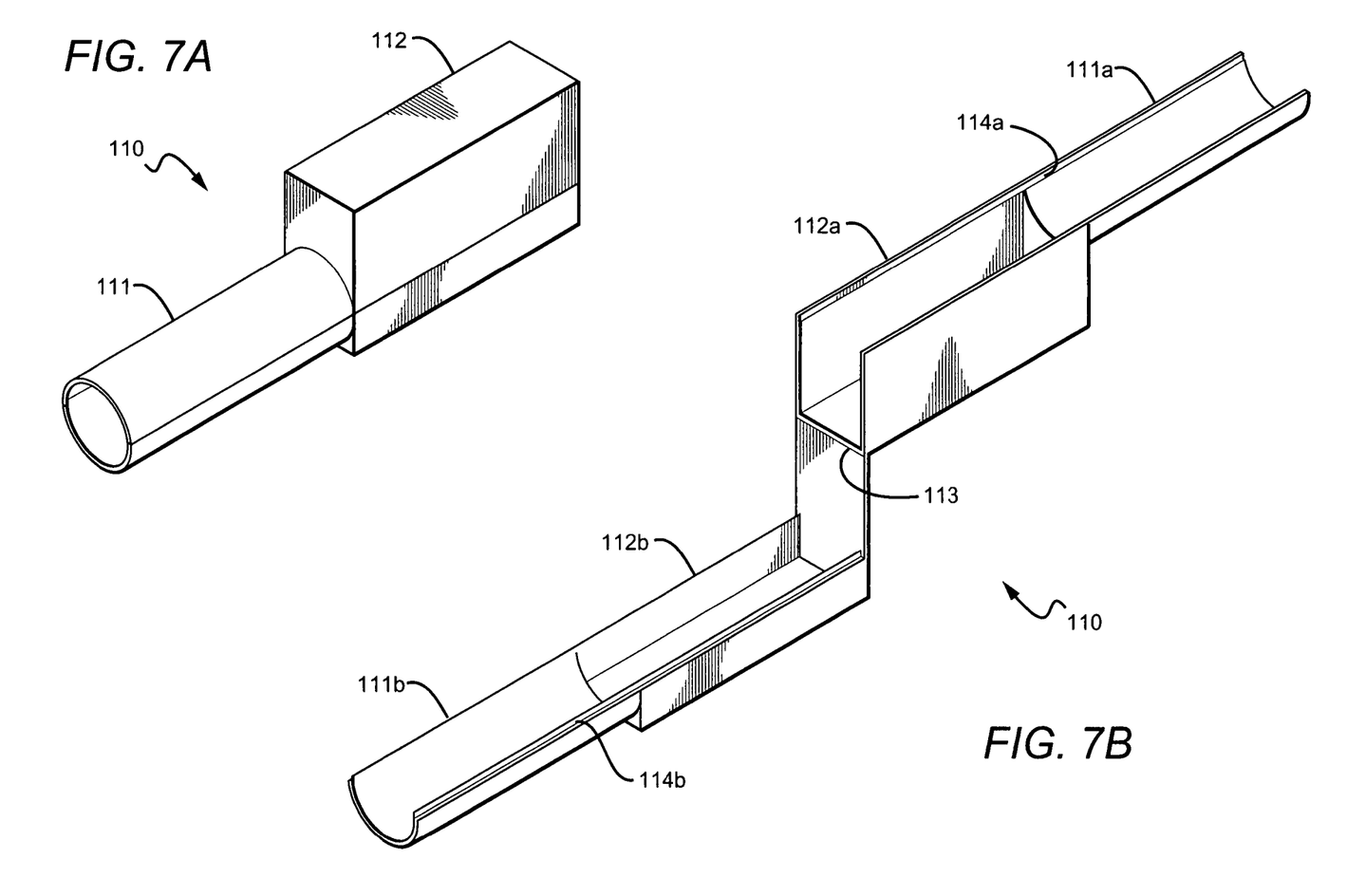
FIG. 7A is a schematic perspective view of one embodiment of the invention showing a encapsulating case for a self-decontaminating brush, the case having a closed position.
FIG. 7B is a schematic perspective view of the embodiment shown in FIG. 7A having an open position.

FIGS. 7A-B show a closed and open variant, respectively, of one type of encapsulating case (enclosure) suitable for use with a self-decontaminating brush according to the invention such as those illustrated in FIGS. 1-2. In the closed position shown in FIG. 7A, the brush head section (112) of the case (110) can envelope, and therefore contain the atmosphere around, the brush head (12) of the brush (10). The handle section (111) of the case (110) can similarly envelope the handle (11), or suitable portion thereof, of the brush (10). The brush (10) can be removed after decontamination (e.g. for storage and/or use) by opening the case (110) as shown in FIG. 7B. In order to facilitate facile and repetitious opening and closing of the case (110) in this embodiment, the brush head section (112) of the case (110) can be fabricated as an upper (112a) and a lower (112b) portion which can be flexibly connected by a living hinge (113). The handle section (111) adjacent to the brush head section (112) can be similarly fabricated as an upper (111a) and a lower (11b) portion. The case (110) can be held together during use by any suitable mechanical or physical means, including without limitation an interlocking tongue (114a) in groove (114b) connection as illustrated in FIG. 7B. In other embodiments, the shape of the encapsulating case can vary according to the shape of the object or surface to be decontaminated and the photocatalytic material and light emitting member used for decontamination. Any suitable material can be used to fabricate such a case, including without limitation polypropylene.

The embodiments and examples set forth herein were presented to explain the nature of the present invention and its practical application, and thereby to enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. One skilled in the art will recognize, for example, that the dimensions, structure, composition, or configuration of the system components disclosed, and the types of objects rendered self-decontaminating by such systems, may vary and accordingly are not to be construed as limiting the scope of the invention.

I claim:

1. A system for self-decontaminating at least one surface of an object, the system comprising:
    at least one support plate;
    at least one photocatalytic material;
    at least one light emitting member capable of generating ozone; and
    a reflective element mounted on, or within, the object and positioned between the at least one light emitting member and the at least one photocatalytic material and is optically connected to the at least one photocatalytic material and the at least one light emitting member, the reflective element being further positioned within a light path of the at least one light emitting member, wherein the reflective element has a length that is approximately equal to the at least one support plate and is configured to direct light emitted by the at least one light emitting member directly at the at least one surface of the object;
    wherein the at least one photocatalytic material and the at least one light emitting member are mounted on, or within, the object,
    wherein the at least one photocatalytic material is optically connected to the at least one light emitting member, and
    wherein the at least one photocatalytic material is adjacent to the at least one surface and is disposed on the at least one support plate for facilitating self-decontamination of the object.

2. The system of claim 1, wherein the object is functionally independent of the system.

3. The system of claim 1, wherein the at least one photocatalytic material comprises titanium dioxide and is capable of generating oxidizing species.

4. The system of claim 1, wherein the at least one light emitting member provides ultraviolet light.

5. The system of claim 4, wherein the at least one light emitting member provides ultraviolet light having a wavelength in a range of about 180 nm to about 425 nm.

6. The system of claim 1, wherein the at least one light emitting member comprises at least one light emitting diode.

7. The system of claim 1, further comprising at least one adhesive material.

8. The system of claim 1, wherein the system is activated on demand.

9. The system of claim 8, wherein the system is activated by at least one control switch.

10. The system of claim 9, wherein the at least one control switch is electrically connected to the at least one light emitting member, and
    wherein the at least one light emitting member provides a quantity of light to the at least one photocatalytic material upon activation of the at least one control switch.

11. An object comprising at least one system according to claim 1.

12. The object of claim 11, wherein the object is at least one of a brush, a toilet plunger holder, and a tape measure.

13. The system of claim 1, the reflective element comprises a reflective surface having a length that is approximately equal to a length of the at least one support plate.

14. The system of claim 13, wherein the at least one reflective surface is positioned at an angle relative to the at least one support plate.

15. The system of claim 1, wherein the object comprises bristles extending from a surface of the object, where the length of the reflective element is approximately equal to a length of an area of the surface from which the bristles extend.

16. A system for self-decontaminating at least one surface of an object, the system comprising:
    at least one support plate;
    at least one photocatalytic material;
    at least one light emitting member capable of generating ozone;
    at least one adhesive material; and at least one reflective element mounted on, or within, the object and positioned between the at least one light emitting member and the at least one photocatalytic material, wherein the at least one reflective element is optically connected to the at least one photocatalytic material and the at least one light emitting member, the at least one reflective element being further positioned within a light path of the at least one light emitting member, where the at least one reflective element is configured to direct light emitted by the at least one light emitting member directly at the at least one surface of the object, and where the at least one reflective element has a length approximately equal to a length of the at least one support plate;

wherein the at least one photocatalytic material and the at least one light emitting member are mounted on, or within, the object, wherein the at least one photocatalytic material is optically connected to the at least one light emitting member, wherein the at least one photocatalytic material is adjacent to the at least one surface and is disposed on the at least one support plate for facilitating self-decontamination of the object, wherein the object is functionally independent of the system, wherein the at least one photocatalytic material comprises titanium dioxide and is capable of generating oxidizing species, wherein the at least one light emitting member provides ultraviolet light, wherein the at least one light emitting member provides ultraviolet light having a wavelength in a range of about 180 nm to about 425 nm, wherein the at least one light emitting member comprises at least one light emitting diode, wherein the system is activable in a manner selected from a group consisting essentially of being activable on demand and being activable by at least one control switch, wherein the at least one control switch is electrically connected to the at least one light emitting member, and wherein the at least one light emitting member provides a quantity of light to the at least one photocatalytic material upon activation of the at least one control switch.

17. The system of claim 16, wherein the at least one reflective element comprises a reflective surface that is positioned at an angle relative to the at least one support plate.

\* \* \* \* \*